(12) United States Patent
Bernard et al.

(10) Patent No.: US 8,500,807 B2
(45) Date of Patent: *Aug. 6, 2013

(54) PHOTOCHROMIC INTRAOCULAR LENS

(75) Inventors: Pascal Bernard, Nieul sur Mer (FR); Marc Dolatkhani, Cestas (FR); Anne Pagnoux, Le Barp (FR); Christophe Hupin, Salles (FR)

(73) Assignee: Carl Zeiss Meditec SAS, Perigny (FR)

( * ) Notice: Subject to any disclaimer, the term of this patent is extended or adjusted under 35 U.S.C. 154(b) by 276 days.

This patent is subject to a terminal disclaimer.

(21) Appl. No.: 11/813,531

(22) PCT Filed: Jan. 6, 2006

(86) PCT No.: PCT/FR2006/000029
§ 371 (c)(1),
(2), (4) Date: Mar. 21, 2008

(87) PCT Pub. No.: WO2006/072748
PCT Pub. Date: Jul. 13, 2006

(65) Prior Publication Data
US 2008/0200983 A1    Aug. 21, 2008

(30) Foreign Application Priority Data

Jan. 7, 2005 (FR) ..................................... 05 00199

(51) Int. Cl.
*A61F 2/16* (2006.01)
*C07D 311/74* (2006.01)
*C07D 311/92* (2006.01)
*C08F 24/00* (2006.01)
*C08F 34/02* (2006.01)

(52) U.S. Cl.
USPC .......... 623/6.56; 526/266; 526/268; 526/280; 526/310; 526/313; 526/328; 526/328.5; 528/405; 528/417; 528/421; 549/385; 549/388; 549/389; 549/390

(58) Field of Classification Search
USPC ................. 526/266, 268, 280, 310, 313, 328, 526/328.5; 528/405, 417, 421; 549/385, 549/388, 389, 390; 623/6.56
See application file for complete search history.

(56) References Cited

U.S. PATENT DOCUMENTS

| 4,871,363 | A | * | 10/1989 | Kelman | ................ 623/6.54 |
| 6,113,814 | A | | 9/2000 | Gemert et al. | |
| 6,224,210 | B1 | | 5/2001 | Chateau et al. | |
| 2001/0025948 | A1 | * | 10/2001 | Walters et al. | ............... 252/586 |
| 2004/0186241 | A1 | * | 9/2004 | Gemert | ................ 525/329.7 |
| 2010/0317805 | A1 | * | 12/2010 | Gibanel et al. | ............... 525/284 |

FOREIGN PATENT DOCUMENTS

| FR | 2870540 A1 | * | 11/2005 |
| WO | WO 0130866 | * | 5/2005 |

OTHER PUBLICATIONS

"UV-blue-light-absorbing photochromic intraocular lens for protection against age-related macular degeneration development," P. Zack et al., Institute for Nanotechnologies of International Conversion Foundation, SPIE, vol. 3579, XP-002341284.

* cited by examiner

*Primary Examiner* — Richard A Huhn
(74) *Attorney, Agent, or Firm* — Young & Thompson

(57) ABSTRACT

The invention relates to an intraocular lens comprising at least one pharmaceutically-acceptable photochromic polymer that enables all or part of the intraocular lens to change colour reversibly when exposed to light.

11 Claims, 1 Drawing Sheet

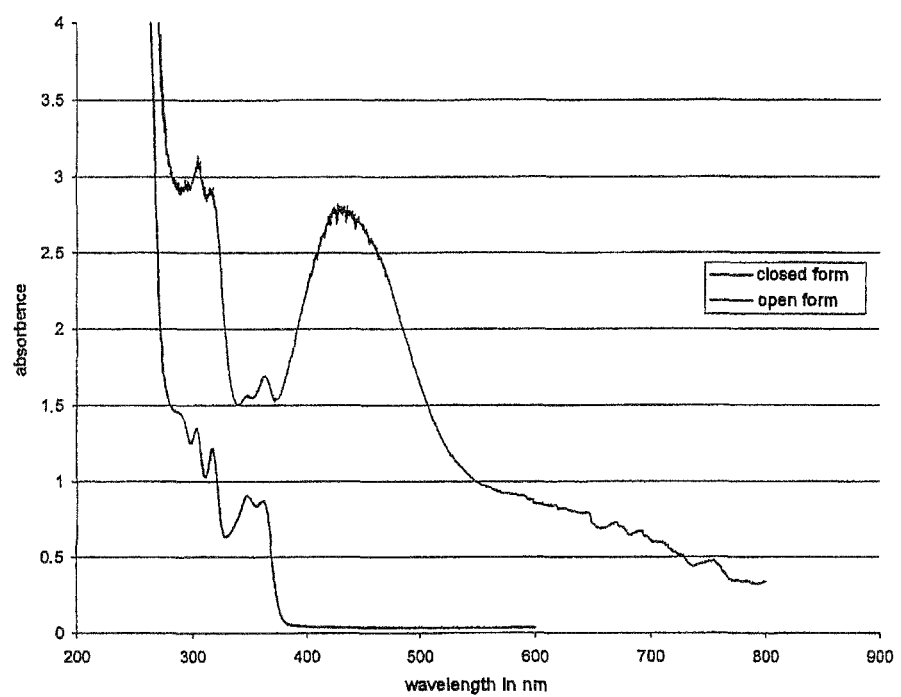

PHOTOCHROMIC INTRAOCULAR LENS

The present invention relates to a hydrophilic or hydrophobic, flexible or rigid capsular intraocular lens consisting, at least in part, of a copolymer which has photochromic monomer units such that the implant, or a part thereof, changes color reversibly when exposed to light, for example to ultraviolet rays.

The crystalline lens is a lens contained in a sac, called the capsular sac, located behind the iris. Cataracts consist of an opacification of the crystalline lens.

A known cataract operation consists in cutting a large part of the anterior wall, called the anterior capsule, of the capsular sac and extracting the crystalline lens therefrom. The extracted crystalline lens is then replaced, in the capsular sac, with an intraocular lens.

The intraocular lenses can be in the form of a "rigid" implant or a "flexible" implant.

The "flexible" implants have the advantage of being easier to position and to stabilize in the capsular sac than rigid implants.

The flexible implants generally consist of a central optical part forming the lens and of a haptic part comprising one or more haptics, located at the periphery of the optical element. These haptic elements may be annular, flat or in the form of loops.

The use of colored materials for manufacturing intraocular lenses has already been envisaged for the purpose of remedying certain transient or permanent problems with vision.

Such problems have in particular been described by H. R. Taylor et al. (Department of Opthalmology, Royal and Victorian Hospital Melbourne) who have shown the involvement of exposure of the retina to an intense blue color (wavelength between 450 and 500 mm) in pterygium and droplet keratopathy.

Colored intraocular lenses have the effect of absorbing certain wavelength ranges, in particular ultraviolet (hereinafter referred to as "UV") ranges and blue ranges.

Such colored intraocular lenses are, for example, described in French Patent Application No. 0215454 filed on 6 Dec. 2002 by the company IOLTECHNOLOGIE-PRODUCTION.

Patent Application EP-A-589 809 describes intraocular lenses in which the coloration is produced using a light transmission adjuvant, i.e. a colorant biocompatible with the internal medium of the human eye.

U.S. Pat. No. 5,662,707 describes intraocular lenses in which the coloration is produced using a polymerizable powder introduced during the constitution of the polymer used to manufacture the intraocular lens.

However, these intraocular lenses have the drawback of reducing visual perception when luminosity drops. Thus, passing from a light zone to a dark zone creates an impairment for the individual wearing the intraocular lens.

The inventors have therefore sought to develop intraocular lenses which make it possible to protect the retina against attack by light rays, in particular blue rays (wavelengths of 450 to 500 nm) and UV rays (wavelengths of between 200 and 380 nm), overcoming the drawbacks of the known lenses.

Such lenses should also be pharmaceutically acceptable, i.e. should consist of materials that are acceptable to the organism and which do not release any compounds which are toxic or aggressive with respect to the tissues.

Thus, the invention consists of an intraocular lens, characterized in that it comprises at least one pharmaceutically acceptable photochromic polymer that allows all or part of said intraocular lens to change color reversibly when exposed to light.

FIG. 1 represents the spectrum of absorbence of the methacrylic photochrome monomer, a preferred photochromic polymer than can be used according to the invention.

Photochromic compounds are materials well known for changing color when exposed to light, in particular to ultraviolet rays.

The inventors have favored photochromic compounds which change color reversibly when exposed to light, in particular to ultraviolet rays.

Such compounds are known as such and used in many applications, in particular in the optical field, where they have been used to brown glasses for sunglasses or to change the color of contact lenses.

An intraocular lens according to the invention can comprise an optical part and a haptic part consisting of one or more elements, the optical part at least comprising a pharmaceutically acceptable photochromic polymer, such that the intraocular lens, or at least its optical part, can change color reversibly.

Said polymer generally comprises at least one photochromic monomer and at least one other monomer which is non-photochromic The photochromic monomer can in particular be of spiro-indolino-spiran, spirobenzothiazolo-benzopyran, spiroindolino-benzothiopyran, spiro-indolino-oxazine or naphthopyran type.

Photochromic monomers that are most particularly suitable for producing intraocular lenses according to the present invention have been described in French Patent Application No. 0405516, filed on 24 May 2004, in the name of the company Polymerexpert.

They are compounds of the polymerizable substituted 3,3-diaryl-3H-naphtho[2,1-b]pyran type, of formula (I):

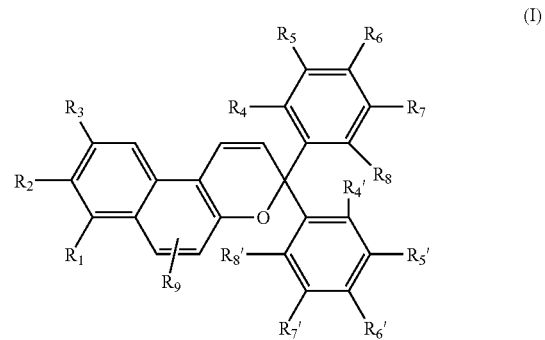

in which

R$_1$, R$_2$ and R$_3$ are such that:
  either at least one of them comprises a divalent group (co)polymerizable with a monomer, the other group(s) R$_1$, R$_2$ and R$_3$ being chosen from the group consisting of hydrogen, halogens, hydroxyl, C$_1$ to C$_{15}$ alkyls, C$_1$ to C$_{15}$ hydroxyalkyls, C$_1$ to C$_{15}$ alkoxy, isocyanates, and groups bearing a carboxylic acid or a silane,
  or at least two of them comprise at least one monovalent group (co)polymerizable with a monomer, the third group being, where appropriate, chosen from the group consisting of hydrogen, halogens and C$_1$ to C$_{15}$ alkyls, $R_4$ to $R_8$ and $R'_4$ to $R'_8$ are identical or different and independently represent a hydrogen, a halogen, a hydroxyl, a $C_1$ to $C_{15}$ alkyl group, a $C_1$ to $C_{15}$ hydroxyalkyl or a $C_1$ to $C_{15}$ alkoxy, $R_9$ represents a hydrogen, a hydroxyl, a $C_1$ to $C_{15}$ alkyl or a $C_1$ to $C_{15}$ hydroxyalkyl.

The compounds of formula (I) have the particularity of having, on the benzene ring of the naphthenic group furthest from the pyran ring, substituents capable of allowing these compounds to participate in chain- or step-(co)polymerization reactions with a monomer. This is made possible by the fact that the $R_1$, $R_2$ and $R_3$ groups are such that at least one is a divalent group (co)polymerizable with a monomer, or that at least two of these groups comprise a monovalent group (co)polymerizable with a monomer.

When the polymerizable group is divalent, the incorporation and then the anchoring of the photochromic monomer in the material is carried out by chain polymerization (anionic polymerization, cationic polymerization, radical polymerization, ring-opening polymerization, metathesis). The other $R_1$, $R_2$ and $R_3$ groups inert with respect to the chain-polymerization mechanism can be chosen from alkyls, hydrogen, halogens, hydroxyls, alkoxy, amines, carboxylic acids, isocyanates, silanes, which cannot react with the divalent polymerizable group. They can be activated, a posteriori, for post-crosslinking by polycondensation or polyaddition or else for a further grafting reaction.

When the polymerizable group is monovalent, the synthesis of the photochromic polymer is carried out by step polymerization between monomers or oligomers which are difunctional, i.e. which bear at least two monovalent substituents. Polyurethanes, polyesters, polyethers, polyamides or polysiloxanes can then in particular be formed by polycondensation or polyaddition. The remaining inert group should be non-reactive with respect to the step-polymerization mechanism and is chosen from hydrogen, alkyls or halogens.

In the specific case of cyclic anhydride and primary amine divalent groups, the polymerization follows a step mechanism; the anchoring of the photochromic monomer is carried out by polycondensation or polyaddition of a photochromic monomer of formula (I), in which at least one of the substituents $R_1$, $R_2$ and $R_3$ bears at least one anhydride or primary amine group, with a difunctional monomer or oligomer.

In formula (I), the groups $R_4$ to $R_8$ and $R'_4$ to $R'_8$ are advantageously independently chosen from the group consisting of hydrogen, methyl, methoxy and fluorine, and $R_9$ is advantageously hydrogen.

Depending on the nature of the polymerizable functions borne by the naphthenic ring, the photochromic monomers of formula (I) can be involved in chain-polymerization or step-polymerization reactions.

More specifically, the monomer of formula (I) can be involved in a chain-polymerization reaction, either when it is in the form of a copolymerizable divalent monomer, or when it is in the form of a copolymerizable tetravalent monomer which can then serve as a crosslinking agent.

An example of a case where the monomer of formula (I) behaves as a copolymerizable divalent monomer is that where one of the groups $R_1$, $R_2$ and $R_3$ comprises a vinyl function, an epoxide group, a (meth)acryloxy- group, a primary amino-group or an anhydride, and the other two are chosen from a hydrogen, a halogen, a hydroxyl, a $C_1$ to $C_{15}$ alkyl group, a $C_1$ to $C_{15}$ hydroxyalkyl group, a $C_1$ to $C_{15}$ alkoxy group.

An example of a case where the monomer of formula (I) behaves as a copolymerizable tetravalent monomer is that where two of the groups $R_1$, $R_2$ and $R_3$ comprise a vinyl function, an epoxide, a meth(acryloxy) group, a primary amino-, an anhydride, and the third group is a hydrogen, a halogen, a hydroxyl, a $C_1$ to $C_{15}$ alkyl group, a $C_1$ to $C_{15}$ hydroxyalkyl group.

In the two cases above, one or two of the groups $R_1$, $R_2$ and $R_3$ are advantageously chosen from the group consisting of —$(C_nH_{2n})$—OC(=O)CH=CH$_2$, —$(C_nH_{2n})$—OC(=O)C(CH$_3$)=CH$_2$, —$(C_nH_{2n})$—O—$(CH)_{n'}$—CH=CH$_2$, —$(C_nH_{2n})$—O—CH=CH$_2$, and the other groups $R_1$, $R_2$ and $R_3$ are H, $(C_nH_{2n})$—CH$_3$, $(C_nH_{2n})$—OH, n and n' being between 0 and 15.

Moreover, the monomers of formula (I) can be involved in step-polymerization reactions, in particular when they are in the form of (co)polyermizable divalent monomers, i.e. they bear two monovalent groups, or of copolymerizable trivalent monomers that can serve as a crosslinking agent.

An example of such (co)polymerizable divalent monomers is that of the monomers of formula (I) in which two of the groups $R_1$, $R_2$ and $R_3$ comprise a hydroxyl, a group bearing a carboxylic acid, a $C_1$ to $C_{15}$ hydroxyalkyl, an isocyanato-, an epoxide, an amino-, an anhydride, or a reactive silane group, it being possible for these two groups to be identical or different, and the third group is chosen from a hydrogen, a $C_1$ to $C_{15}$ alkyl and a halogen.

An example of a copolymerizable trivalent monomer of formula (I) is that in which the three groups $R_1$, $R_2$ and $R_3$ are chosen independently from the group consisting of hydroxyls, hydroxyalkyls, isocyanato-groups, an anhydride, epoxides, amino-groups, groups bearing a carboxylic acid, and groups bearing a reactive silane (Si—H or Si—C=C).

As a preferred monomer of formula (I) comprising at least two polymerizable monovalent groups, mention may be made of those in which at least two of the groups $R_1$, $R_2$ and $R_3$ are chosen from the groups —$(c_nH_{2n})$—OH, —$(C_nH_{2n})$—NH$_2$, —$(C_nH_{2n})$—[CH—CH$_2$—O]ring, —$(C_nH_{2n})$—COOH, —$(C_nH_{2n})$—Si $(C_mH_{2m})_2$—H and —$(C_nH_{2n})$—Si—CHCH$_2$, —$(C_nH_{2n})$—Si—(O—$C_mH_{2m})_3$, —$(C_nH_{2n})$—O—C(=O)NH—$R_{10}$—N=C=O, with $R_{10}$ being chosen from —$(C_nH_{2n})$, —$(C_nH_{2n-2})$, —$(C_nH_{2n-2})$—CH$_2$—$(C_nH_{2n-2})$, aryl or aryl-CH$_2$-aryl, n being between 0 and 15, m being between 1 and 15, and the aryl groups comprising from 5 to 20 carbon atoms; the remaining group, if there is one, being H or a $C_1$ to $C_{15}$ alkyl.

Among these compounds, those comprising three groups $R_1$, $R_2$ and $R_3$ chosen independently from the groups as defined above, make it possible to have copolymerizable trivalent monomers that can serve as a crosslinking agent.

As regards the monomers of formula (I) comprising two polymerizable monovalent groups $R_1$, $R_2$ and $R_3$, it should be noted that the polymerizable functions can be either of the same nature or of different nature, for example:
- a hydroxyalkyl and an amine group, the third group being hydrogen or an alkyl group,
- a hydroxyalkyl group and a group bearing a carboxylic acid, the third group being either hydrogen or an alkyl group,
- a group bearing a carboxylic acid and an amine group, the third group itself being either hydrogen or an alkyl.

According to a most particularly preferred aspect of the invention, said photochromic monomer corresponds to the formula:

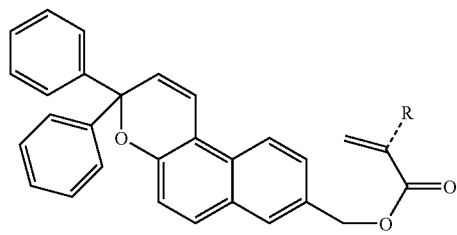

in which R represents H or CH$_3$.

The compounds of formula (I) described above can be prepared by a synthetic process which comprises a cyclization step that will be referred to hereinafter as chromenization step, during which an intermediate product corresponding to formula II below:

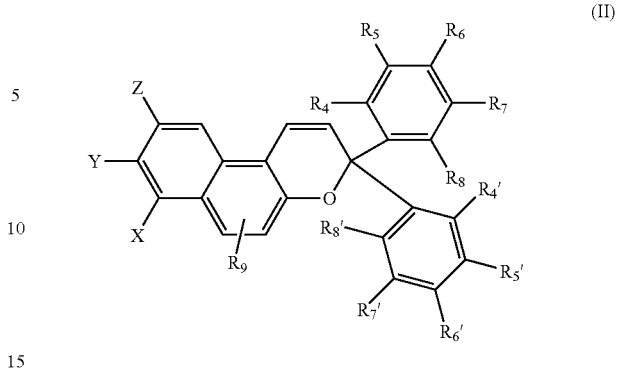

in which the groups X, Y, Z are either the groups $R_1$, $R_2$ and $R_3$ as defined above, or optionally protected precursors of these groups, the various groups $R_4$ to $R_9$ and $R'_4$ to $R'_8$ being as defined above, is precipitated.

The complete synthesis scheme (synthesis scheme No. 1) for the preferred monomers of the invention, in which the group $R_2$ is a divalent polymerizable group of (meth)acrylic type, is given below:

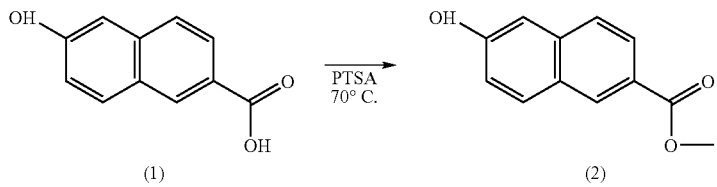

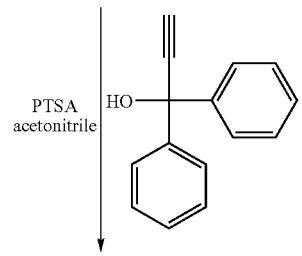

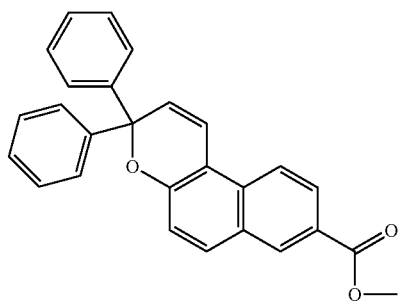

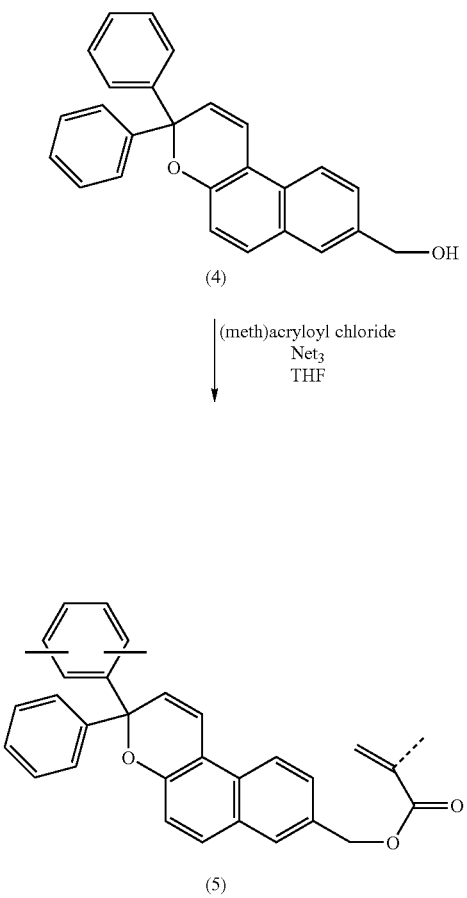

As appears on the synthesis scheme above, which is the subject of a detailed description in Examples 1 and 2 which follow, the final product (product 5) is obtained in steps that are completely industrializable due to the good yield from each of these steps and the purity of the products obtained.

The product (3) can be isolated particularly simply and effectively by simple filtration due to the choice of the reaction medium in which the cyclization (chromenization) for synthesizing it from the compound (2) of the preceding step is carried out.

This cyclization step, during which the intermediate desired for the subsequent steps is precipitated, proves to be a key step of the process.

This is because many of the monomers of formula (I) described above can be produced from this product (3).

In fact, in the case of the above scheme, the compound (3) is subjected to a reduction step so as to produce the product (4) which then undergoes grafting.

Those skilled in the art will readily understand, in view of this scheme, that other "deprotection" steps can be envisaged, for example the hydrolysis of the ester function so as to obtain a carboxylic acid or else the controlled reduction of the ester to aldehyde.

Other grafting steps can also be envisaged, for example the reaction of the hydroxylated product (4) with a diisocyanate so as to obtain a photochrome with a reactive isocyanate function or else the functionalization of the product (4) by means of a transetherification reaction with an enolyl ether in the presence of mercury acetate so as to produce a vinyl function.

Moreover, those skilled in the art will readily understand that, in a scheme similar to that represented above, an epoxy-group can be obtained by reaction of the compound (4) with epichlorohydrin.

Thus, by means of a scheme similar to that presented above, it is possible to obtain all the monomers of formula (I) which have a polymerizable divalent group, from a commercial product such as the product (I) or from products derived from this product, for which, for example, the group $R_1$ or $R_3$ bears a $CO_2H$ group.

As regards the monomers of the invention comprising two monovalent groups, they can be obtained by following the synthesis scheme below (synthesis scheme No. 2) or a scheme derived therefrom, that can be readily envisaged by those skilled in the art.

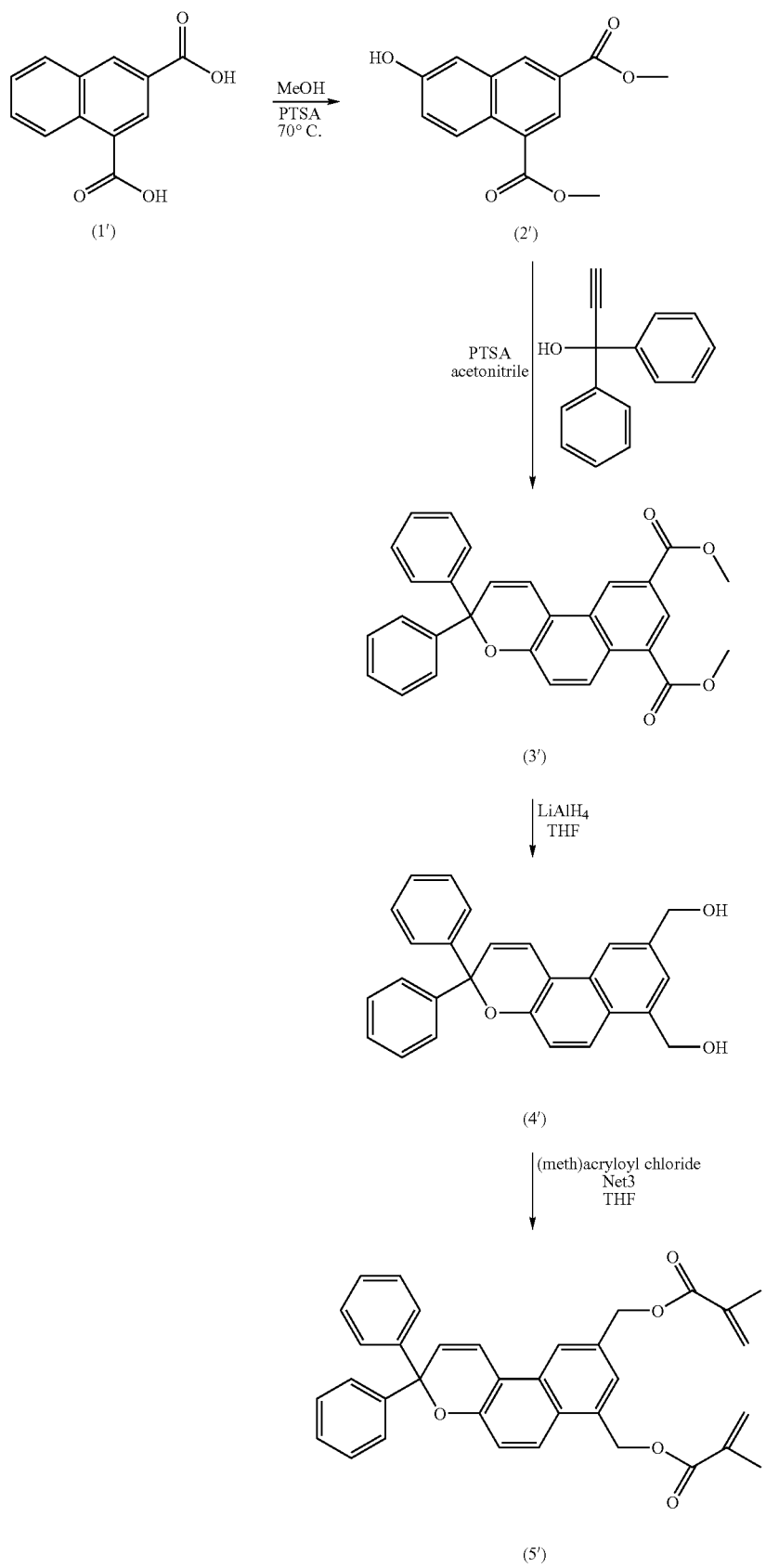

As in the previous case, other types of functions can be envisaged; thus, the hydroxyl group of the compound (4') can be converted to an amine or the ester (3') can be hydrolyzed to a carboxylic acid.

In addition to the photochromic monomer(s), the polymer according to the invention can be formed from at least one other monomer, which is non-photochromic, of formula (III)

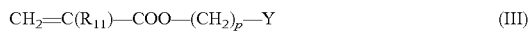

in which:

$R_{11}$ is H or $CH_3$, p is 0-10,

Y is chosen from the group consisting of: hydrogen; OH; a $C_1$-$C_{10}$ hydroxyalkyl group; a $C_1$-$C_{10}$ fluoroalkyl group; a $C_1$-$C_{10}$ alkoxy group; a $C_1$-$C_{10}$ acyloxy group; a $C_1$-$C_{10}$ acylamino group; a $C_1$-$C_{10}$ alkylsulfinyl group; a $C_1$-$C_{10}$ alkylsulfonyl group; a residue —($CH_2$—$CH_2$—O)$_t$—H where t is between 1 and 100; a residue Ar or W-Ar, Ar representing an aromatic ring, in particular phenyl, where appropriate substituted with a $C_1$-$C_8$ alkyl group, a chlorine atom or a bromine atom, and W representing O, S or $NR_{12}$, $R_{12}$ being H or a $C_1$-$C_{10}$ alkyl group.

The monomer of formula (III) is preferably chosen from the group consisting of an alkyl methacrylate, preferably methyl methacrylate, a hydroxyalkyl methacrylate, a hydroxyalkyl acrylate, a phenoxyalkyl acrylate and a phenoxyalkyl methacrylate.

More preferably, the monomer of formula (III) is hydroxyethyl methacrylate or 2-phenoxyethyl methacrylate.

According to an advantageous aspect of the invention, the polymer forming all or part of the intraocular lens comprises:
a photochromic monomer consisting of 3,3-diphenyl-3H-naphtho[2,1]pyran methacrylate, 3,3-diphenyl-3H-naphtho[2,1]pyran acrylate or a mixture of these monomers, and
hydroxyethyl methacrylate or 2-phenoxyethyl methacrylate.

The polymers in accordance with the invention can be obtained by copolymerization of a photochromic monomer, in particular a monomer of formula (I) described above, with at least one non-photochromic monomer, in particular a monomer of formula (III) described above.

The polymerization can be carried out according to any conventional method, in particular those indicated above, for example chain polymerization (anionic polymerization, cationic polymerization, radical polymerization, ring-opening polymerization, metathesis polymerization) or step polymerization.

The polymerization can be carried out in the presence of a crosslinking agent, such as diacrylates and dimethacrylates of bisphenol A ethoxylate (1 EO/phenol), bisphenol A ethoxylate (2 EO/phenol), bisphenol A propoxylate (2 PO/phenol), bisphenol A, 2,2'-diallylbisphenol A or bis(4-(2-methacryloyl-ethoxy)phenyl)methane.

The polymerization could be carried out in the presence of polymerization-initiating compounds which could be added to the monomers, in particular peroxides, peroxydicarbonates, free azo radicals, especially 2,2-azobisisobutyronitrile.

Usually, a polymer constituting an intraocular lens according to the invention comprises a proportion of photochromic monomers in said polymer of between 0.01% and 5%, preferably between 0.02% and 2% (proportion by mass).

The polymerization can be carried out directly in a mould such that the polymer is recovered in the form of a blank for an intraocular lens.

This blank can then be made into the form of an intraocular lens according to conventional methods for those skilled in the art, for example by machining or cryomachining on a lathe. The polymers used in the context of the invention are, when they are excited by light, preferably yellow to orange in color.

When the light decreases, the polymer loses its color. Under these conditions, the intraocular lens of the invention, completely or partially comprising such a polymer, makes it possible to protect the retina against light rays, in particular blue rays and UV rays, while at the same time allowing vision of good quality when the light intensity decreases.

The aim of the examples which follow is to illustrate the invention.

EXAMPLES

Example 1

Synthesis of 8-hydroxymethyl-3,3-diphenyl-3H-naphtho[2,1]pyran (compound (4))

This example is given with reference to synthesis scheme No. 1, described above.

Step 1: Esterification of the Compound (1)

The compound (1) (7 g) is dissolved in 80 ml of methanol, in a three-necked round-bottomed flask (250 ml) surmounted by a condenser. The esterification reaction is catalyzed by the addition of para-toluenesulfonic acid (PTSA, 0.48 g) introduced under nitrogen. The reaction is brought to a temperature of 70° C. and is left stirring for at least 12 hours.

At the end of this period, the methanol is evaporated off and the residual organic phase is dissolved in ethyl acetate for the purpose of liquid/liquid extractions (ethyl acetate/potassium carbonate-saturated water) in order to purify the expected ester (compound (2)).

The organic phase resulting from the various washes is then dried over $MgSO_4$ and then filtered. Evaporation of the ethyl acetate makes it possible to quantitatively isolate the desired ester (6 to 7 g).

Step 2: Chromenization of Compound (2)

1.56 g of compound (2) are introduced with 50 ml of acetonitrile into a three-necked round-bottomed flask (100 ml) surmounted by a condenser.

The medium becomes clear as soon as the temperature reaches 50° C., at which time 1.6 g (1 eq/(2)) of propargyl alcohol and 0.122 g of PTSA (0.08 eq/(2)) are added under nitrogen. The reaction medium is cooled to ambient temperature and stirred for two days at this temperature.

Compound (3) is simply isolated by filtration since it is insoluble in the reaction medium. It is purified by washes in acetonitrile at 40° C. followed by filtrations. The product is obtained with a yield of 55% without further purification.

Step 3: Reduction of the Ester (3) to Obtain (4): 8-Hydroxymethyl-3,3-diphenyl-3H-naphtho[2,1]pyran 0.2 g of $LiAlH_4$ (1.41 eq/(3)) diluted in 15 ml of anhydrous THF is introduced into a three-necked round-bottomed flask (100 ml) equipped with a bubbler. The 1.5 g (3) dissolved in 30 ml of anhydrous THF are then added, under nitrogen and dropwise. During the addition, no violent release of gas 20 is observed. The whole is stirred for at least 12 hours at ambient temperature.

Before isolating the product (4), the excess $LiAlH_4$ must be neutralized. To do this, 1.25 ml of water and then 12.5 ml of a 10% solution of sulfuric acid ($H_2SO_4$) are added slowly. The addition of ether to the medium causes two phases to emerge.

The extracted organic phase is washed (NaCl-saturated water) and then dried with MgSO$_4$ and filtered and the solvent is evaporated off.

The white product obtained with a quantitative yield corresponds to the expected compound (4).

Example 2

Functionalization with Acryloyl Chloride: Compound (5)

1 g of compound 4, and 0.5 ml of Et$_3$N (1.3 eq/(4)) dissolved in 30 ml of anhydrous THF are introduced into a three-necked round-bottomed flask (100 ml) surmounted by a condenser. The addition of the chloride is carried out dropwise, under nitrogen, at ambient temperature, without any substantial increase in temperature being observed. The reaction is left at ambient temperature for at least 12 hours, with stirring.

At the end of this period, the solvent is evaporated off. The residue is diluted in dichloromethane and then extracted by successive washes with potassium carbonate-saturated water. The extracted organic phase is dried with MgSO$_4$ and filtered over silica, and the solvent is evaporated off.

3,3-Diphenyl-3H-naphtho[2,1]pyran acrylate is isolated with a mass yield of 60%.

Example 3

Functionalization with Methacryloyl Chloride

The synthesis is identical to that of Example 2, except that the acryloyl chloride is replaced with methacryloyl chloride.

3,3-Diphenyl-3H-naphtho[2,1]pyran methacrylate is thus obtained.

Example 4

Production of a Photochromic Polymer for Use as a Starting Material for Intraocular Lenses, from the Monomer of Example 2

72.439 g of distilled hydroxyethyl methacrylate, followed by 10.06 g of distilled methyl methacrylate, and also 0.210 g of ethylene glycol dimethacrylate are introduced into a glass tube. The chosen initiator is 2,2-azobisisobutyronitrile, which is solubilized in the mixture of monomer (0.167 g). 0.041 g of 3,3-diphenyl-3H-naphtho[2,1]pyran methacrylate (product of Example 2) is added to the reaction medium. The latter is placed under an inert atmosphere and is subjected to the following temperature cycle: 24 h at 48° C., 9 h at 80° C. and 3 h of post-curing at 90° C.

Example 5

Production of a Photochromic Polymer for Use as a Starting Material for Intraocular Lenses, from the Monomer of Example 2

72.439 g of distilled hyroxyethyl methacrylate, followed by 10.06 g of distilled methyl methacrylate, and also 0.210 g of ethylene glycol dimethacrylate, are introduced into a glass tube. The chosen initiator is 2,2-azobisisobutyronitrile, which is solubilized in the mixture of monomer (0.167 g) with 0.04 g of 3,3-diphenyl-3H-naphtho[2,1]pyran acrylate (product of Example 2).

The latter is placed under an inert atmosphere and is subjected to the following temperature cycle: 24 h at 48° C., 9 h at 80° C. and 3 h of post-curing at 90° C.

The polymer obtained has, after hydration, a water content of 28%. It is colorless, but when subjected to sunlight, it reversibly develops a yellow color.

The polymer was subjected to closed-form and open-form absorbence tests. The results obtained are represented in FIG. 1.

Example 6

Production of a Photochromic Polymer for Use as a Starting Material for Intraocular Lenses, from the Monomer of Example 3

82 g of methyl methacrylate and 0.21 g of ethylene glycol dimethacrylate are introduced into a glass tube. The chosen initiator is 2,2-azobisisobutyronitrile solubilized in the mixture of monomer (0.167 g) with 0.04 g of 3,3-diphenyl-3H-naphtho[2,1]pyran methacrylate (product of Example 3).

Example 7

Production of a Photochromic Polymer for Use as Starting Material for Intraocular Lenses, from the Monomer of Example 2

550.0 g of 2-phenoxyethyl methacrylate, 0.286 g of 3,3-diphenyl-3H-naphtho[2,1]pyran (product of Example 2) and 716.15±10.0 mg of 2,2'-azobisisobutyronitrile are introduced into a three-necked round-bottomed flask (2 l). Once the solid particles have dissolved in the liquid monomer, the mixture is stirred at 800 rpm under nitrogen for 45 minutes at ambient temperature. The temperature of the mixture is then brought to 45±2° C. and the stirring speed is gradually decreased to 150 rpm as the viscosity of the mixture increases. When disappearance of the vortex is observed, the polymerization is stopped by rapidly cooling the reaction medium with liquid nitrogen. When the mixture has returned to ambient temperature, 27.8 g of bisphenol ethoxylate (2 EO/phenol) dimethacrylate are added thereto. The reaction medium is kept at ambient temperature for 2 h, with stirring. The mixture is then degassed under vacuum for 5 h before being filtered.

The mixture is then brought to a temperature of 118° C. for 13 hours and then 135° C. for 3 hours.

The invention claimed is:

1. An intraocular lens, comprising at least one pharmaceutically acceptable photochromic polymer that allows all or part of said intraocular lens to change color reversibly when exposed to light, wherein said photochromic polymer is formed from at least one photochromic monomer which is a compound of the polymerizable substituted 3,3-diaryl-3H-naphtho [2,1-b]pyran type, of formula (I):

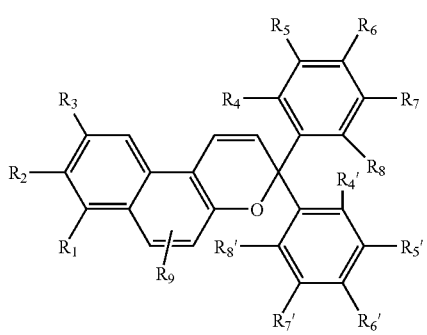

(I)

in which

R$_1$, R$_2$ and R$_3$ are chosen independently from the group consisting of hydroxyls, hydroxylalkyls, isocyanato-groups, an anhydride, epoxides, amino- groups, groups bearing a carboxylic acid, and groups bearing a reactive silane, R$_4$ to R$_8$ and R$_4'$ to R$_8'$ are identical or different and independently represent a hydrogen, a halogen, a hydroxyl, a C$_1$ to C$_{15}$ alkyl, a C$_1$ to C$_{15}$ hydroxyalkyl or a C$_1$ to C$_{15}$ alkoxy, and R$_9$ represents a hydrogen, a hydroxyl, a C$_1$ to C$_{15}$ alkyl or a C$_1$ to C$_{15}$ hydroxyalkyl.

2. The intraocular lens according to claim 1, further comprising an optical part and a haptic part consisting of one or more elements, the optical part at least comprising said pharmaceutically acceptable photochromic polymer.

3. The intraocular lens according to claim 1, wherein, in formula (I), R$_4$ to R$_8$ and R$_4'$ to R$_8'$ are identical or different and independently represent a hydrogen, a methyl, a methoxy or fluorine and R$_9$ is hydrogen.

4. The intraocular lens according to claim 1, wherein at least two of the groups R$_1$, R$_2$ and R$_3$ are chosen from the groups —(C$_n$H$_{2n}$)—OH, —(C$_n$H$_{2n}$)—NH$_2$, —(C$_n$H$_{2n}$)—[CH—CH$_2$—O]ring, —(C$_n$H$_{2n}$)—COOH, —(C$_n$H$_{2n}$)—Si(C$_m$H$_{2m}$)$_2$—H and —(C$_n$H$_{2n}$)—Si—CHCH$_2$ , —(C$_n$H$_{2n}$)—Si—(O—C$_m$H$_{2m}$)$_3$, and —(C$_n$H$_{2n}$)—O—C(=O)NH—R$_{10}$—N=C=O, with:

R$_{10}$=—(C$_n$H$_{2n}$) , —(C$_n$H$_{2n-2}$) , —(C$_n$H$_{2n2}$)—CH$_2$—(C$_n$H$_{2n-2}$) , aryl or aryl-CH$_2$-aryl, n being between 0 and 15, m being between 1 and 15, and the aryl groups comprising from 5 to 20 carbon atoms.

5. The intraocular lens according to claim 4, wherein the groups R$_1$, R$_2$ and R$_3$ are chosen independently from the groups —(C$_n$H$_{2n}$)—OH, —(C$_n$H$_{2n}$)—NH$_2$ , —(C$_n$H$_{2n}$)—[CH—CH$_2$—O]ring, —(C$_n$H$_{2n}$)—COOH, —(C$_m$H$_{2m}$)$_2$—H and —(C$_n$H$_{2n}$)—Si—CH=CH$_2$, —(C$_n$H$_{2n}$)—Si—(O—C$_m$H$_{2m}$) $_3$, and —(C$_m$H$_{2m}$)—O—C(=O)NH—R$_{10}$—N=C=O, with:

R$_{10}$=—(C$_n$H$_{2n}$) or —(C$_n$H$_{2n-2}$) or —(C$_n$H$_{2n-2}$)—CH$_2$—(C$_n$H$_{2n-2}$) , aryl or aryl-CH$_2$-aryl, n being between 0 and 15, m being between 1 and 15 and the aryl groups comprising from 5 to 20 carbon atoms.

6. The intraocular lens according to claim 1, wherein said polymer is also formed from at least one non-photochromic monomer of formula (III)

$$CH_2=C(R_{11})-COO-(CH_2)_p-Y \quad (III)$$

in which:

R$_{11}$ is H or CH$_3$, p is 0-10,

Y is chosen from the group consisting of: hydrogen; OH; a C$_1$-C$_{10}$hydroxyalkyl group; a C$_1$-C$_{10}$ fluoroalkyl group; a C$_1$-C$_{10}$ alkoxy group; a C$_1$-C$_{10}$acyloxy group; a C$_1$-C$_{10}$acylamino group; a C$_1$-C$_{10}$alkylsulfinyl group; a C$_1$-C$_{10}$alkylsulfonyl group; a residue —(CH$_2$—CH$_2$—O)$_t$—H where t is between 1 and 100; a residue Ar or W—Ar, Ar representing an aromatic ring, in particular phenyl, where appropriate substituted with a C$_1$-C$_8$ alkyl group, a chlorine atom or a bromine atom, and W representing O, S or NR$_{12}$, R$_{12}$ being H or a C$_1$-C$_{10}$alkyl group.

7. The intraocular lens according to claim 6, wherein the monomer of formula (III) is chosen from the group consisting of:

an alkyl methacrylate, a hydroxyalkyl methacrylate, a hydroxyalkyl acrylate, a phenoxyalkyl acrylate and a phenoxyalkyl methacrylate.

8. The intraocular lens according to claim 7, wherein the monomer of formula (III) is hydroxyethyl methacrylate or 2-phenoxyethyl methacrylate.

9. The intraocular lens according to claim 1, wherein the proportion of the photochromic monomer in the polymer is between 0.01% and 5%, proportion by mass.

10. An intraocular lens comprising at least one pharmaceutically acceptable photochromic polymer that allows all or part of said intraocular lens to change color reversibly when exposed to light, wherein said photochromic polymer is formed from at least one photochromic monomer which is a compound of the polymerizable substituted 3,3-diaryl-3H-naphtho[2,1-b]pyran type, of formula:

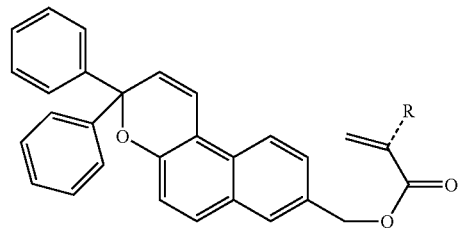

in which R represents H or CH$_3$.

11. The intraocular lens according to claim 10, wherein said polymer comprises:

a photochromic monomer consisting of (3,3-diphenyl-3H-naphtho[2,1-b]pyran)methyl methacrylate, (3,3-diphenyl-3H-naphtho[2,1-b]pyran)methyl acrylate, or a mixture of these monomers, and a non-photochromic monomer consisting of hydroxyethyl methacrylate or 2-phenoxyethyl methacrylate.

* * * * *

UNITED STATES PATENT AND TRADEMARK OFFICE
CERTIFICATE OF CORRECTION

PATENT NO. : 8,500,807 B2  Page 1 of 1
APPLICATION NO. : 11/813531
DATED : August 6, 2013
INVENTOR(S) : Bernard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 621 days.

Signed and Sealed this
Fifteenth Day of September, 2015

Michelle K. Lee
*Director of the United States Patent and Trademark Office*